(12) United States Patent
Takahata et al.

(10) Patent No.: US 9,089,482 B2
(45) Date of Patent: Jul. 28, 2015

(54) DENTAL MILL BLANK

(75) Inventors: Yusuke Takahata, Kurashiki (JP); Michiya Kawana, Kurashiki (JP)

(73) Assignee: KURARAY NORITAKE DENTAL INC., Kurashiki-shi (JP)

( * ) Notice: Subject to any disclaimer, the term of this patent is extended or adjusted under 35 U.S.C. 154(b) by 0 days.

(21) Appl. No.: 13/820,764

(22) PCT Filed: Sep. 30, 2011

(86) PCT No.: PCT/JP2011/005560
§ 371 (c)(1),
(2), (4) Date: Mar. 5, 2013

(87) PCT Pub. No.: WO2012/042911
PCT Pub. Date: Apr. 5, 2012

(65) Prior Publication Data
US 2013/0172441 A1   Jul. 4, 2013

(30) Foreign Application Priority Data

Sep. 30, 2010 (JP) ................... 2010-221378

(51) Int. Cl.
| *A61K 6/083* | (2006.01) |
| *C08L 33/10* | (2006.01) |
| *A61C 13/00* | (2006.01) |
| *A61K 6/00* | (2006.01) |
| *A61K 6/027* | (2006.01) |

(52) U.S. Cl.
CPC .............. *A61K 6/083* (2013.01); *A61C 13/0022* (2013.01); *A61K 6/0008* (2013.01); *A61K 6/0276* (2013.01)

(58) Field of Classification Search
None
See application file for complete search history.

(56) References Cited

U.S. PATENT DOCUMENTS

| 4,567,030 | A   | 1/1986  | Yuasa et al. |
| 4,719,297 | A   | 1/1988  | Henne et al. |
| 4,764,497 | A   | 8/1988  | Yuasa et al. |
| 5,744,511 | A   | 4/1998  | Kazama et al. |
| 5,990,195 | A   | 11/1999 | Arita |
| 8,436,078 | B2* | 5/2013  | Okubayashi et al. ......... 523/216 |
| 8,440,739 | B2  | 5/2013  | Okubayashi et al. |
| 2003/0036582 | A1  | 2/2003  | Yamakawa et al. |
| 2003/0162863 | A1  | 8/2003  | Satoh et al. |
| 2005/0009946 | A1  | 1/2005  | Oguri et al. |
| 2005/0253130 | A1  | 11/2005 | Tsutsumi et al. |
| 2011/0046260 | A1* | 2/2011  | Okubayashi et al. ......... 523/115 |
| 2011/0065828 | A1  | 3/2011  | Okubayashi et al. |
| 2011/0257292 | A1  | 10/2011 | Okubayashi et al. |
| 2013/0049241 | A1* | 2/2013  | Tsujimoto .................. 264/19 |

FOREIGN PATENT DOCUMENTS

| CA | 2051333          | 9/1996 |
| CA | 2 722 653 A1     | 11/2009 |
| CA | 2 722 661 A1     | 11/2009 |
| EP | 0 009 348        | 7/1983 |
| EP | 2 380 551 A1     | 10/2011 |
| GB | 2 115 799 A      | 9/1983 |
| JP | 57 197289        | 12/1982 |
| JP | 58 110414        | 7/1983 |
| JP | 58-110414 A      | 7/1983 |
| JP | 9 3109           | 1/1997 |
| JP | 9-169613 A       | 6/1997 |
| JP | 10 245525        | 9/1998 |
| JP | 10 323353        | 12/1998 |
| JP | 2000 159621      | 6/2000 |
| JP | 2002-255722 A    | 9/2002 |
| JP | 2003 96122       | 4/2003 |
| JP | 2003 529386      | 10/2003 |
| JP | 2005-310756 A    | 11/2005 |
| WO | WO 02/05752 A1   | 1/2002 |
| WO | 2009 133913      | 11/2009 |
| WO | WO 2009/133913 A1 | 11/2009 |
| WO | 2009 154301      | 12/2009 |
| WO | WO 2011/074222 A1 | 6/2011 |

OTHER PUBLICATIONS

Technical Information 1251: Aerosil and Sipernat Silica, Evonik Industries, May 2012.*
International Search Report Issued Dec. 20, 2011 in PCT/JP11/05560, Filed Sep. 30, 2011.
Extended European Search Report issued Mar. 3, 2014, in Patent Application No. 11828476.9.

* cited by examiner

*Primary Examiner* — James J Seidleck
*Assistant Examiner* — Peter A Salamon
(74) *Attorney, Agent, or Firm* — Oblon, McClelland, Maier & Neustadt, L.L.P.

(57) ABSTRACT

The present invention provides a dental mill blank having excellent mechanical strength and having gloss retention high enough to maintain the gloss similar to that of natural teeth in an oral cavity for a long period of time. The present invention is a dental mill blank made of a cured product of a curable composition containing: a polymerizable monomer (A); and a spherical inorganic filler (B) having an average primary particle size of not less than 0.1 µm and less than 1 µm.

5 Claims, No Drawings

DENTAL MILL BLANK

TECHNICAL FIELD

The present invention relates to a dental mill blank suitable for use in fabricating dental prostheses such as inlays and crowns by machining in a CAD/CAM system.

BACKGROUND ART

In recent years, CAD/CAM systems have been widely used to design dental prostheses such as inlays and crowns by computers to fabricate them by machining with milling machines. Conventionally, with the emphasis on the aesthetic appearance, ceramic materials are generally used as materials for mill blanks to be machined in these systems. However, since ceramics are very hard and brittle materials, dental prostheses fabricated from ceramic mill blanks have problems such as damage to the opposing teeth and cracking caused by impact of machining or occlusion.

In order to solve these problems, mill blanks made of composite materials containing polymer resins and fillers, being hard but not so hard as to damage the opposing teeth, and having excellent impact resistance have recently been developed and used in clinical practice.

For example, Patent Literature 1 describes a mill blank containing a polymer resin and a filler, for use in fabricating a dental prosthesis. For the filler, a filler obtained by finely grinding a material obtained by the sol-gel method, a commercially available irregular-shaped barium glass filler, a filler obtained by grinding quartz with a mill, and an ultrafine particle inorganic filler (average particle size of 40 nm) are studied.

Patent Literature 2 describes a mill blank containing an acrylic resin polymer and an ultrafine particle inorganic filler having an average particle size of 0.01 to 0.04 µm, for use in fabricating a dental prosthesis.

CITATION LIST

Patent Literature

Patent Literature 1: JP 2003-529386 T
Patent Literature 2: JP 10 (1998)-323353 A

SUMMARY OF INVENTION

Technical Problem

In the case where a ground-type filler or an irregular-shaped barium glass filler as described in Patent Literature 1 is used for a mill blank, the resulting mill blank has high mechanical strength but low gloss retention. Therefore, when the mill blank is used in an oral cavity for a long period of time, its gloss is likely to decrease and thus its aesthetic properties are at an unsatisfactory level.

In the case where an ultrafine particle inorganic filler as described in Patent Literature 1 or 2 is used for a mill blank, the resulting mill blank has high gloss retention and excellent aesthetic properties. However, since the particles of the ultrafine inorganic filler are too small to increase its content, the mechanical strength of the mill blank is not high enough. Patent Literature 2 also describes the combined use of an irregular-shaped glass powder to increase the mechanical strength. However, the gloss retention decreases and thus the aesthetic properties are at an unsatisfactory level.

The present invention has been made in order to solve the above conventional problems, and it is an object of the present invention to provide a dental mill blank having excellent mechanical strength and having gloss retention high enough to maintain the gloss similar to that of natural teeth in an oral cavity for a long period of time.

Solution to Problem

The present invention is a dental mill blank made of a cured product of a curable composition containing: a polymerizable monomer (A); and a spherical inorganic filler (B) having an average primary particle size of not less than 0.1 µm and less than 1 µm.

In the present invention, it is preferable that the spherical inorganic filler (B) be composed of: silica particles; particles of an oxide of at least one metal selected from the group consisting of Group 2, Group 4, Group 12 and Group 13 metals of the periodic table; or particles of a composite oxide containing a silicon atom, an oxygen atom, and an atom of at least one metal selected from the group consisting of Group 2, Group 4, Group 12 and Group 13 metals of the periodic table. Preferably, the polymerizable monomer (A) is a (meth) acrylic acid ester. Preferably, the curable composition contains 65 to 900 parts by weight of the spherical inorganic filler (B) per 100 parts by weight of the polymerizable monomer (A).

In a preferred embodiment of the dental mill blank of the present invention, the curable composition further contains an inorganic ultrafine particle aggregate filler (C) composed of aggregates of inorganic ultrafine particles having an average primary particle size of 2 to 50 nm. The polymerizable monomer (A) has a refractive index of 1.52 to 1.58 after polymerization, the spherical inorganic filler (B) has a refractive index of 1.52 to 1.58, and the inorganic ultrafine particle aggregate filler (C) has a refractive index of 1.43 to 1.50. The content of the inorganic ultrafine particle aggregate filler (C) in the curable composition is 0.1 to 10% by weight.

Advantageous Effects of Invention

Machining of the dental mill blank of the present invention using a CAD/CAM system makes it possible to provide an aesthetic dental prosthesis having high mechanical/physical properties and excellent gloss retention.

DESCRIPTION OF EMBODIMENTS

The dental mill blank of the present invention is obtained by polymerizing/curing a curable composition containing a polymerizable monomer (A) and a spherical inorganic filler (B) as components. As used in the present invention, a "dental mill blank" refers to a solid block of a material from which a dental prosthesis can be fabricated by processing such as cutting, carving or milling.

As the polymerizable monomer (A) used in the present invention, any known polymerizable monomers used for dental curable compositions, etc. can be used without any limitation, and generally, a radical polymerizable monomer is used suitably. Specific examples of the radical polymerizable monomer in the polymerizable monomer (A) include esters of α-cyanoacrylic acid, (meth)acrylic acid, α-halogenated acrylic acid, crotonic acid, cinnamic acid, sorbic acid, maleic acid, itaconic acid, etc., (meth)acrylamide, (meth)acrylamide derivatives, vinyl esters, vinyl ethers, mono-N-vinyl derivatives, styrene derivatives, and the like. Among them, (meth) acrylic acid esters and (meth)acrylamide derivatives are preferred, and (meth)acrylic acid esters are more preferred. In the present invention, "(meth)acryl" means methacryl or acryl.

Examples of (meth)acrylic acid ester-based and (meth)acrylamide derivative-based polymerizable monomers are given hereinbelow.

(1) Monofunctional (Meth)Acrylates and (Meth)Acrylamide Derivatives Include:

methyl(meth)acrylate, isobutyl(meth)acrylate, benzyl (meth)acrylate, lauryl(meth)acrylate, 2-(N,N-dimethylamino)ethyl(meth)acrylate, 2,3-dibromopropyl(meth)acrylate, 2-hydroxyethyl(meth)acrylate, 6-hydroxyhexyl(meth)acrylate, 10-hydroxydecyl(meth)acrylate, propylene glycol mono(meth)acrylate, glycerol mono(meth)acrylate, erythritol mono(meth)acrylate, N-methylol(meth)acrylamide, N-hydroxyethyl(meth)acrylamide, N-(dihydroxyethyl) (meth)acrylamide, (meth)acryloyloxydodecylpyridinium bromide, (meth)acryloyloxydodecylpyridinium chloride, (meth)acryloyloxyhexadecylpyridinium chloride, (meth)acryloyloxydecylammonium chloride, 2-(meth)acryloyloxyethyl dihydrogen phosphate, 10-(meth)acryloyloxydecyl dihydrogen phosphate, 2-(meth)acryloyloxyethyl phenylhydrogen phosphate, 11-(meth)acryloyloxy-1,1-undecanedicarboxylic acid, 4-(meth)acryloyloxyethoxycarbonyl phthalic acid, 10-mercaptodecyl(meth)acrylate, and the like.

(2) Bifunctional (Meth)Acrylates Include:

ethylene glycol di(meth)acrylate, triethylene glycol di(meth)acrylate, propylene glycol di(meth)acrylate, neopentyl glycol di(meth)acylate, 1,6-hexanediol di(meth)acrylate, 1,10-decanediol di(meth)acrylate, bisphenol A diglycidyl(meth)acrylate (2,2-bis[4-[3-(meth)acryloyloxy-2-hydroxypropoxy]phenyl]propane (commonly known as "BisGMA")), 2,2-bis[4-(meth)acryloyloxyethoxyphenyl]propane, 2,2-bis[4-(meth)acryloyloxypolyethoxyphenyl]propane, 1,2-bis[3-(meth)acryloyloxy-2-hydroxypropoxy]ethane, pentaerythritol di(meth)acrylate, [2,2,4-trimethylhexamethylenebis(2-carbamoyloxyethyl)]dimethacrylate (commonly known as "UDMA"), and the like.

(3) Trifunctional or Higher Polyfunctional (Meth)Acrylates Include:

trimethylolpropane tri(meth)acrylate, trimethylolethane tri(meth)acrylate, tetramethylolmethane tri(meth)acrylate, pentaerythritol tetra(meth)acrylate, dipentaerythritol hexa(meth)acrylate, N,N'-(2,2,4-trimethylhexamethylene)bis[2-(aminocarboxy)propane-1,3-diol]tetramethacrylate, 1,7-diacryloyloxy-2,2,6,6-tetraacryloyloxymethyl-4-oxyheptane, and the like.

Any of the above-mentioned polymerizable monomers can be used alone or as a mixture of two or more kinds thereof.

As the spherical inorganic filler (B) used in the present invention, any known spherical inorganic fillers used in dental curable compositions, etc. can be used without any limitation as long as they have average primary particle sizes of not less than 0.1 μm and less than 1 μm. "Spherical" fillers include nearly spherical fillers, and they do not necessarily have to be perfectly spherical. Generally, when a micrograph of particles is taken with a scanning electron microscope, 30 particles are selected arbitrarily from the particles observed within a unit field of view of the micrograph, and then the aspect ratio of each of the particles is calculated by dividing the length of the particle in the direction orthogonal to its maximum length by the maximum length, the average thereof (average aspect ratio) is preferably 0.6 or more, more preferably 0.8 or more, and particularly preferably 0.9 or more.

As the spherical inorganic filler (B), silica particles; particles of an oxide of at least one metal selected from the group consisting of Group 2, Group 4, Group 12 and Group 13 metals of the periodic table; or particles of a composite oxide containing a silicon atom, an oxygen atom and an atom of at least one metal selected from the group consisting of Group 2, Group 4, Group 12 and Group 13 metals of the periodic table are suitably used. Specific examples of these include particles of amorphous silica, quartz, cristobalite, and tridymite; alumina, titanium dioxide, strontium oxide, barium oxide, zinc oxide, zirconium oxide, and hafnium oxide; silica-zirconia, silica-titania, silica-titania-barium oxide, silica-alumina, silica-titania-sodium oxide, silica-titania-potassium oxide, silica-zirconia-sodium oxide, silica-zirconia-potassium oxide, silica-barium oxide, and silica-strontium oxide; and the like. As the spherical inorganic filler (B), silica particles; particles of an oxide of a Group 4 metal of the periodic table; or particles of a composite oxide containing a silicon atom, an oxygen atom and an atom of a Group 4 metal of the periodic table are more suitably used. Particles of silica-zirconia are further suitably used because the resulting mill blank has radiopacity and better abrasion resistance. Hydroxyapatite also can be used as the spherical inorganic filler.

The spherical inorganic filler (B) has an average primary particle size of not less than 0.1 μm and less than 1 μm. When the average primary particle size is less than 0.1 μm, the resulting dental mill blank cannot have sufficient mechanical strength. On the other hand, when the average primary particle size is 1 μm or more, the resulting dental mill blank cannot have sufficient gloss retention. The average primary particle size is preferably 0.1 to 0.5 μm, and more preferably 0.1 to 0.3 μm. The average particle size of the spherical inorganic filler (B) can be determined by the laser diffraction/scattering method. More specifically, for example, the average particle size can be determined by the measurement using a 0.2% aqueous solution of sodium hexametaphosphate as a dispersion medium, with a laser diffraction particle size distribution analyzer (SALD-2100, manufactured by Shimadzu Corporation).

As the spherical inorganic filler (B), the above particles may be used alone or in appropriate combination of two or more different kinds of particles having different compositions.

The spherical inorganic filler (B) is used in combination with the polymerizable monomer (A). Therefore, it is desirable that the spherical inorganic filler (B) be previously subjected to surface treatment with a surface treating agent to improve the affinity between the spherical inorganic filler (B) and the polymerizable monomer (A), and to increase the chemical bonding between the spherical inorganic filler (B) and the polymerizable monomer (A) so as to enhance the mechanical strength of the resulting cured product. As such a surface treating agent, an organometallic compound such as an organosilicon compound, an organotitanium compound, an organozirconium compound or an organoaluminum compound, or an acidic group-containing compound having at least one acidic group such as a phosphoric acid group, a pyrophosphoric acid group, a thiophosphoric acid group, a phosphonic acid group, a sulfonic acid group or a carboxylic acid group can be used. When two or more kinds of surface treating agents are used, the surface-treated layer may be made of a mixture of these two or more kinds of surface treating agents, or may have a multilayer structure in which a plurality of surface-treated layers are laminated. As for the method of surface treatment, any known method can be used without any particular limitation.

An example of the organosilicon compound is a compound represented by $R^1{}_n SiX_{4-n}$ (where $R^1$ is a substituted or unsubstituted hydrocarbon group having 1 to 12 carbon atoms, X is an alkoxy group having 1 to 4 carbon atoms, a hydroxyl group, a halogen atom, or a hydrogen atom, and n is an integer of 0 to 3. If a plurality of $R^1$s and a plurality of Xs are present, the $R^1$s may be the same as or different from one another, and the Xs may be the same as or different from one another.)

Specific examples of the organosilicon compound include methyltrimethoxysilane, dimethyldimethoxysilane, phenyltrimethoxysilane, diphenyldimethoxysilane, methyltriethoxysilane, dimethyldiethoxysilane, phenyltriethoxysilane, diphenyldiethoxysilane, isobutyltrimethoxysilane, vinyltrimethoxysilane, vinyltriethoxysilane, vinyl-tris(β-methoxyethoxy)silane, 3,3,3-trifluoropropyl trimethoxysilane, methyl-3,3,3-trifluoropropyl dimethoxysilane, β-(3,4-epoxycyclohexyl)ethyltrimethoxysilane, γ-glycidoxypropyltrimethoxysilane, γ-glycidoxypropylmethyldiethoxysilane, γ-glycidoxypropyltriethoxysilane, γ-methacryloxypropylmethyldimethoxysilane, γ-methacryloxypropylmethyldiethoxysilane, N-β(aminoethyl)γ-aminopropylmethyldimethoxysilane, N-β(aminoethyl)γ-aminopropyltrimethoxysilane, N-β(aminoethyl)γ-aminopropyltriethoxysilane, γ-aminopropyltrimethoxysilane, γ-aminopropyltriethoxysilane, N-phenyl-γ-aminopropyltrimethoxysilane, γ-mercaptopropyltrimethoxysilane, trimethylsilanol, methyltrichlorosilane, methyldichlorosilane, dimethyldichlorosilane, trimethylchlorosilane, phenyltrichlorosilane, diphenyldichlorosilane, vinyltrichlorosilane, trimethylbromosilane, diethylsilane, vinyltriacetoxysilane, ω-(meth)acryloxyalkyl trimethoxysilane (having 3 to 12 carbon atoms between a (meth)acryloxy group and a silicon atom, for example, γ-methacryloxypropyltrimethoxysilane, or the like), ω-(meth)acryloxyalkyl triethoxysilane (having 3 to 12 carbon atoms between a (meth)acryloxy group and a silicon atom, for example, γ-methacryloxypropyltriethoxysilane, or the like), and the like. In the present invention, "(meth)acryloxy" means methacryloxy or acryloxy.

Among them, a coupling agent having a functional group that is copolymerizable with the above-mentioned polymerizable monomer (A), for example, ω-(meth)acryloxyalkyl trimethoxysilane (having 3 to 12 carbon atoms between a (meth)acryloxy group and a silicon atom), ω-(meth)acryloxyalkyl triethoxysilane (having 3 to 12 carbon atoms between a (meth)acryloxy group and a silicon atom), vinyltrimethoxysilane, vinyltriethoxysilane, vinyltriacetoxysilane, γ-glycidoxypropyltrimethoxysilane, or the like is used preferably.

Examples of the organotitanium compound include tetramethyl titanate, tetraisopropyl titanate, tetra-n-butyl titanate, butyl titanate dimmer, and tetra(2-ethylhexyl)titanate.

Examples of the organozirconium compound include zirconium isopropoxide, zirconium-n-butoxide, zirconium acetylacetonate, and zirconyl acetate.

Examples of the organoaluminum compound include aluminum acetylacetonate, and a chelate compound of a salt of aluminum and an organic acid.

Examples of the acidic group-containing organic compound containing a phosphoric acid group include 2-ethylhexyl acid phosphate, stearyl acid phosphate, 2-(meth)acryloyloxyethyl dihydrogen phosphate, 3-(meth)acryloyloxypropyl dihydrogen phosphate, 4-(meth)acryloyloxybutyl dihydrogen phosphate, 5-(meth)acryloyloxypentyl dihydrogen phosphate, 6-(meth)acryloyloxyhexyl dihydrogen phosphate, 7-(meth)acryloyloxyheptyl dihydrogen phosphate, 8-(meth)acryloyloxyoctyl dihydrogen phosphate, 9-(meth)acryloyloxynonyl dihydrogen phosphate, 10-(meth)acryloyloxydecyl dihydrogen phosphate, 11-(meth)acryloyloxyundecyl dihydrogen phosphate, 12-(meth)acryloyloxydodecyl dihydrogen phosphate, 16-(meth)acryloyloxyhexadecyl dihydrogen phosphate, 20-(meth)acryloyloxyicosyl dihydrogen phosphate, bis[2-(meth)acryloyloxyethyl]hydrogen phosphate, bis[4-(meth)acryloyloxybutyl]hydrogen phosphate, bis[6-(meth)acryloyloxyhexyl]hydrogen phosphate, bis[8-(meth)acryloyloxyoctyl]hydrogen phosphate, bis[9-(meth)acryloyloxynonyl]hydrogen phosphate, bis[10-(meth)acryloyloxydecyl]hydrogen phosphate, 1,3-di(meth)acryloyloxypropyl dihydrogen phosphate, 2-(meth)acryloyloxyethylphenyl hydrogen phosphate, 2-(meth)acryloyloxyethyl-2-bromoethyl hydrogen phosphate, bis[2-(meth)acryloyloxy-(1-hydroxymethyl)ethyl]hydrogen phosphate, and acid chlorides, alkali metal salts, ammonium salts, etc. thereof.

Examples of the acidic group-containing organic compound containing a pyrophosphoric acid group include bis-octylpyrophosphate, bis[4-(meth)acryloyloxybutyl]pyrophosphate, bis[6-(meth)acryloyloxyhexyl]pyrophosphate, bis[8-(meth)acryloyloxyoctyl]pyrophosphate, bis[10-(meth)acryloyloxydecyl]pyrophosphate, and acid chlorides, alkali metal salts ammonium salts, etc. thereof.

Examples of the acidic group-containing organic compound containing a thiophosphoric acid group include ethyl dihydrogen thiophosphate, 2-(meth)acryloyloxyethyl dihydrogen thiophosphate, 3-(meth)acryloyloxypropyl dihydrogen thiophosphate, 4-(meth)acryloyloxybutyl dihydrogen thiophosphate, 5-(meth)acryloyloxypentyl dihydrogen thiophosphate, 6-(meth)acryloyloxyhexyl dihydrogen thiophosphate, 7-(meth)acryloyloxyheptyl dihydrogen thiophosphate, 8-(meth)acryloyloxyoctyl dihydrogen thiophosphate, 9-(meth)acryloyloxynonyl dihydrogen thiophosphate, 10-(meth)acryloyloxydecyl dihydrogen thiophosphate, 11-(meth)acryloyloxyundecyl dihydrogen thiophosphate, 12-(meth)acryloyloxydodecyl dihydrogen thiophosphate, 16-(meth)acryloyloxyhexadecyl dihydrogen thiophosphate, 20-(meth)acryloyloxyicosyl dihydrogen thiophosphate, and acid chlorides, alkali metal salts, ammonium salts, etc. thereof.

Examples of the acidic group-containing organic compound containing a phosphonic acid group include hexyl-3-phosphonopropyonate, 2-(meth)acryloyloxyethylphenyl phosphonate, 5-(meth)acryloyloxypentyl-3-phosphonopropyonate, 6-(meth)acryloyloxyhexyl-3-phosphonopropyonate, 10-(meth)acryloyloxydecyl-3-phosphonopropyonate, 6-(meth)acryloyloxyhexyl-3-phosphonoacetate, 10-(meth)acryloyloxydecyl-3-phosphonoacetate, and acid chlorides, alkali metal salts, ammonium salts, etc. thereof.

Examples of the acidic group-containing organic compound containing a sulfonic acid group include benzenesulfonic acid, 2-(meth)acrylamide-2-methylpropane sulfonic acid, styrenesulfonic acid, and 2-sulfoethyl(meth)acrylate.

Examples of the acidic group-containing organic compound containing a carboxylic acid group include a compound having one carboxyl group in a molecule and a compound having a plurality of carboxyl groups in a molecule.

Examples of the compound having one carboxyl group in a molecule include octanoic acid, decanoic acid, (meth)acrylic acid, N-(meth)acryloyl glycine, N-(meth)acryloyl aspartic acid, O-(meth)acryloyl tyrosine, N-(meth)acryloyl tyrosine, N-(meth)acryloylphenylalanine, N-(meth)acryloyl-p-aminobenzoic acid, N-(meth)acryloyl-o-aminobenzoic acid, p-vinylbenzoic acid, 2-(meth)acryloyloxybenzoic acid, 3-(meth)acryloyloxybenzoic acid, 4-(meth)acryloyloxybenzoic acid, N-(meth)acryloyl-5-aminosalicylic acid, N-(meth)acryloyl-4-aminosalicylic acid, 2-(meth)acryloyloxyethyl hydrogen succinate, 2-(meth)acryloyloxyethyl hydrogen phthalate, 2-(meth)acryloyloxyethyl hydrogen malate, and acid halides thereof.

Examples of the compound having a plurality of carboxyl groups in a molecule include malonic acid, glutaric acid, 6-(meth)acryloyloxyhexane-1,1-dicarboxylic acid, 9-(meth)acryloyloxynonane-1,1-dicarboxylic acid, 10-(meth)acryloyloxydecane-1,1-dicarboxylic acid, 11-(meth)acryloyloxyundecane-1,1-dicarboxylic acid, 12-(meth)acryloyloxydodecane-1,1-dicarboxylic acid, 13-(meth)acryloyloxytridecane-1,1-dicarboxylic acid, 4-(meth)acryloyloxyethyl trimellitate, 4-(meth)acryloyloxybutyl trimellitate, 4-(meth)acryloyloxyhexyl trimellitate, 4-(meth)acryloyloxydecyl trimellitate, 2-(meth)acryloyloxyethyl-3'-(meth)acryloyloxy-2'-(3,4-dicarboxybenzoyloxy)propyl succinate, and acid anhydrides, acid halides, etc. thereof.

One of the above surface treating agents may be used alone, or two or more thereof may be used in combination. In order to increase the chemical bonding between the spherical inorganic filler (B) and the polymerizable monomer (A) so as to enhance the mechanical strength of the cured product, it is more preferable to use an acidic group-containing organic compound having a functional group that is copolymerizable with the polymerizable monomer (A).

The content of the spherical inorganic filler (B) in the curable composition is preferably 65 to 900 parts by weight per 100 parts by weight of the polymerizable monomer (A), more preferably 100 to 700 parts by weight, and further preferably 120 to 500 parts by weight. When the content of the spherical inorganic filler (B) is less than 65 parts by weight, the resulting dental mill blank may have insufficient mechanical strength and gloss retention. On the other hand, when the content exceeds 900 parts by weight, it may be difficult to mix the polymerizable monomer (A) and the spherical inorganic filler (B).

In the present invention, in order to enhance the color matching between the dental mill blank obtained by curing the curable composition and natural teeth, it is preferable to add an inorganic ultrafine particle aggregate filler (C) composed of aggregates of inorganic ultrafine particles having an average primary particle size of 2 to 50 nm to the curable composition.

As the inorganic ultrafine particles, any known inorganic ultrafine particles used in dental curable compositions, etc. are used without any limitation as long as they have an average primary particle size of 2 to 50 nm. Preferable examples of the inorganic ultrafine particles include particles of inorganic oxides such as silica, alumina, titania, zirconia, particles of composite oxides of any of these oxides, and particles of calcium phosphate, hydroxyapatite, yttrium fluoride, ytterbium fluoride, and the like. Preferably, the inorganic ultrafine particles are particles of silica, alumina, titania, or the like prepared by flame pyrolysis, and examples thereof include products manufactured by Japan Aerosil Co., Ltd. under the trade names of Aerosil, Aeroxide Alu C, Aeroxide $TiO_2$ P 25, Aeroxide $TiO_2$ P 25S, VP Zirconium Oxide 3-YSZ, and VP Zirconium Oxide 3-YSZ PH. The shape of the inorganic ultrafine particles is not particularly limited, and any shape can be selected appropriately for use.

The average primary particle size of the inorganic ultrafine particles is 2 to 50 nm. The use of inorganic ultrafine particles having such an average primary particle size makes it possible to enhance the color matching of the resulting dental mill blank with natural teeth without decreasing the gloss retention of the dental mill blank. The average primary particle size of the inorganic ultrafine particles can be obtained by taking a micrograph of the particles with a scanning electron microscope (H-800NA, manufactured by Hitachi, Ltd.) and measuring the particle size of particles (200 or more) observed in a unit field of view of the micrograph, with an image-analyzing particle size distribution analysis software (Mac-View (Mountech Co., Ltd.)). In this case, the particle size of the particle is obtained as an arithmetic mean value of the longest and shortest dimensions thereof, and the average primary particle size is calculated from the number of the particles and their particle sizes thus obtained.

By virtue of the inorganic ultrafine particles in the form of aggregates, the resulting dental mill blank can have higher transparency, haze and total light transmittance, which are the optical properties required for the improvement of the color matching between the dental mill blank and natural teeth.

Like the spherical inorganic filler (B), the inorganic ultrafine particle aggregate filler (C) is used in combination with the polymerizable monomer (A) for the dental mill blank. Therefore, it is desirable that the inorganic ultrafine particle aggregate filler (C) be previously subjected to surface treatment with a surface treating agent to improve the affinity between the inorganic ultrafine particle aggregate filler (C) and the polymerizable monomer (A), and to increase the chemical bonding between the inorganic ultrafine particle aggregate filler (C) and the polymerizable monomer (A) so as to enhance the mechanical strength of the cured product. As the surface treating agent, any one of the organometallic compounds and the acidic group-containing organic compounds described as examples for the spherical inorganic filler (B) can be used likewise.

In the case where the inorganic ultrafine particle aggregate filler (C) is added to the curable composition, it is preferable that the polymerizable monomer (A) have a refractive index of 1.52 to 1.58 after polymerization, the spherical inorganic filler (B) have a refractive index of 1.52 to 1.58, and the inorganic ultrafine particle aggregate filler (C) have a refractive index of 1.43 to 1.50. The combined use of the polymerizable monomer (A), the spherical inorganic filler (B) and the inorganic ultrafine particle aggregate filler (C) having these refractive indices makes it possible to provide a dental mill blank having excellent color matching with natural teeth. It is more preferable that the polymerizable monomer (A) have a refractive index of 1.53 to 1.56 after polymerization, the spherical inorganic filler (B) have a refractive index of 1.53 to 1.56, and the inorganic ultrafine particle aggregate filler (C) have a refractive index of 1.44 to 1.47. The refractive index of the polymerizable monomer (A) after polymerization refers to the refractive index of the polymer of the polymerizable monomer (A). To obtain a desired refractive index of the polymerizable monomer (A) after polymerization, one kind of polymerizable monomer may be selected, or several kinds of polymerizable monomers having different refractive indices may be mixed at an appropriate ratio, with taking into consideration that a polymer obtained by polymerizing a polymerizable monomer generally tends to have a slightly higher refractive index than the polymerizable monomer itself. The spherical inorganic filler (B) and the inorganic ultrafine particle aggregate filler (C) having the above refractive indices are known.

The content of the inorganic ultrafine particle aggregate filler (C) is preferably 0.1 to 10% by weight in the curable composition, and more preferably 1 to 7% by weight.

In the present invention, the curable composition may further contain a filler other than the spherical inorganic filler (B) and the inorganic ultrafine particle aggregate filler (C) as long as the mechanical strength and gloss retention of the cured product are not decreased. Examples of such a filler include an irregular-shaped inorganic filler having a primary particle size of more than 50 nm, an organic-inorganic composite filler and an organic filler. These fillers may be used alone, or two or more of these may be used in combination.

As the irregular-shaped inorganic filler, any known irregular-shaped inorganic particles used in dental curable compositions, etc. are used without any limitation as long as their primary particle size exceeds 50 nm. Examples of the material of the irregular-shaped inorganic filler include: various kinds of glass powders [containing silica as a main component and further containing an oxide of a heavy metal, boron, aluminum, and the like, if necessary: e.g., glass powders having typical compositions, such as fused silica, quartz, soda lime silica glass, E-glass, C-glass, borosilicate glass (Pyrex (registered trademark) glass); and glass powders for dental use, such as barium glass (GM 27884 and 8235 manufactured by Schott, and Ray-Sorb E-2000 and Ray-Sorb E-3000 manufactured by Specialty Glass), strontium borosilicate glass (Ray-Sorb E-4000 manufactured by Specialty Glass), lanthanum glass ceramics (GM 31684 manufactured by Schott), and fluoroaluminosilicate glass (GM 35429, G018-091, G018-117 manufactured by Schott)]; various kinds of ceramics; composite oxides such as silica-titania, and silica-zirconia; diatomaceous earth; kaolin; clay minerals (such as montmorillonite); activated white clay; synthetic zeolite; mica; calcium fluoride; ytterbium fluoride; yttrium fluoride; calcium phosphate; barium sulfate; zirconium dioxide; titanium dioxide; hydroxyapatite; and the like. Any of the above-mentioned inorganic particles can be used alone or as a mixture of two or more kinds thereof. Among them, those containing silica as a main component (at least 25% by weight of silica, preferably at least 40% by weight of silica) are used suitably.

The above-mentioned irregular-shaped inorganic filler is used in combination with the polymerizable monomer (A) for the dental mill blank. Therefore, it is desirable that the irregular-shaped inorganic filler be previously subjected to surface treatment with a surface treating agent to improve the affinity between the irregular-shaped inorganic filler and the polymerizable monomer (A), and to increase the chemical bonding between the irregular-shaped inorganic filler and the polymerizable monomer (A) so as to enhance the mechanical strength of the cured product. As such a surface treating agent, any one of the organometallic compounds and acidic group-containing organic compounds described as examples for the spherical inorganic filler (B) can be used likewise.

As the organic-inorganic composite filler, any known organic-inorganic composite particles used in dental curable compositions, etc. are used without any limitation. Generally, an organic-inorganic composite filler is obtained by previously adding a polymerizable monomer to the above spherical inorganic filler (B) and/or the above irregular-shaped filler and/or the above inorganic ultrafine particle aggregate filler (C) to obtain a mixture in a paste form, which is then polymerized and ground. The organic-inorganic composite filler that can be used is, for example, a TMPT filler (obtained by mixing trimethylolpropane methacrylate with a silica filler, polymerizing the mixture, and then grinding it). The shape and particle size of the organic-inorganic composite filler are not particularly limited, and any shape and particle size can be selected appropriately for use.

Like the spherical inorganic filler (B), the organic-inorganic composite filler is used in combination with the polymerizable monomer (A) for the dental mill blank. Therefore, it is desirable that the organic-inorganic composite filler be previously subjected to surface treatment with a surface treating agent to improve the affinity between the organic-inorganic composite filler and the polymerizable monomer (A), and to increase the chemical bonding between the organic-inorganic composite filler and the polymerizable monomer (A) so as to enhance the mechanical strength of the cured product. As such a surface treating agent, any one of the organometallic compounds and acidic group-containing organic compounds described as examples for the spherical inorganic filler (B) can be used likewise.

As the organic filler, any known organic particles used in dental curable compositions, etc. are used without any limitation. Examples of the material for this organic filler include polymethyl methacrylate, polyethyl methacrylate, methyl methacrylate-ethyl methacrylate copolymer, cross-linked polymethyl methacrylate, cross-linked polyethyl methacrylate, polyamide, polyvinyl chloride, polystyrene, chloroprene rubber, nitrile rubber, ethylene-vinyl acetate copolymer, styrene-butadiene copolymer, acrylonitrile-styrene copolymer, and acrylonitrile-styrene-butadiene copolymer. These may be used alone or in the form of a mixture of two or more of them. The shape and particle size of the organic filler are not particularly limited, and any shape and particle size can be selected appropriately for use.

The dental mill blank of the present invention is fabricated by polymerizing/curing a curable composition containing the polymerizable monomer (A) and the spherical inorganic filler (B). So, the curable composition may contain a polymerization initiator to facilitate curing through polymerization. The polymerization initiator can be selected from polymerization initiators commonly used in the industrial field. Among them, polymerization initiators used for dental applications are used preferably. Particularly, thermal polymerization initiators, photopolymerization initiators and chemical polymerization initiators are used alone, or two or more of them are used in appropriate combination.

Examples of the thermal polymerization initiators include organic peroxides and azo compounds.

Examples of the organic peroxides used as the above thermal polymerization initiator include ketone peroxide, hydroperoxide, diacyl peroxide, dialkyl peroxide, peroxyketal, peroxyester, peroxydicarbonate, and the like.

Examples of the ketone peroxide used as the above thermal polymerization initiator include methyl ethyl ketone peroxide, methyl isobutyl ketone peroxide, methylcyclohexanone peroxide, cyclohexanone peroxide, and the like.

Examples of the hydroperoxide used as the above thermal polymerization initiator include 2,5-dimethylhexane-2,5-dihydroperoxide, diisopropylbenzene hydroperoxide, cumene hydroperoxide, t-butyl hydroperoxide, and 1,1,3,3-tetramethylbutyl hydroperoxide.

Examples of the diacyl peroxide used as the above thermal polymerization initiator include acetyl peroxide, isobutyryl peroxide, benzoyl peroxide, decanoyl peroxide, 3,5,5-trimethylhexanoyl peroxide, 2,4-dichlorobenzoyl peroxide, and lauroyl peroxide.

Examples of the dialkyl peroxide used as the above thermal polymerization initiator include di-t-butyl peroxide, dicumyl peroxide, t-butylcumyl peroxide, 2,5-dimethyl-2,5-di(t-butylperoxy)hexane, 1,3-bis(t-butylperoxyisopropyl)benzene, and 2,5-dimethyl-2,5-di(t-butylperoxy)-3-hexyne.

Examples of the peroxyketal used as the above thermal polymerization initiator include 1,1-bis(t-butylperoxy)-3,3,5-trimethylcyclohexane, 1,1-bis(t-butylperoxy)cyclohexane, 2,2-bis(t-butylperoxy)butane, 2,2-bis(t-butylperoxy)octane, and 4,4-bis(t-butylperoxy)valeric acid-n-butyl ester.

Examples of the peroxyester used as the above thermal polymerization initiator include α-cumyl peroxyneodecanoate, t-butyl peroxyneodecanoate, t-butyl peroxypivarate, 2,2,4-trimethylpentylperoxy-2-ethyl hexanoate, t-amylperoxy-2-ethyl hexanoate, t-butylperoxy-2-ethyl hexanoate, dit-butylperoxy isophthalate, di-t-butylperoxy hexahydroterephthalate, t-butylperoxy-3,3,5-trimethyl hexanoate, t-butylperoxy acetate, t-butylperoxy benzoate, and t-butylperoxymaleic acid.

Examples of the peroxydicarbonate used as the above thermal polymerization initiator include di-3-methoxy peroxydicarbonate, di-2-ethylhexyl peroxydicarbonate, bis(4-t-butylcyclohexyl)peroxydicarbonate, diisopropyl peroxydicarbonate, di-n-propyl peroxydicarbonate, di-2-ethoxyethyl peroxydicarbonate, and diallyl peroxydicarbonate.

Among these organic peroxides, diacyl peroxides are used preferably from the viewpoint of an overall balance of safety, storage stability, and radical production ability, and among these, benzoyl peroxide is used more preferably.

Examples of the azo compounds used as the above thermal polymerization initiator include 2,2-azobisisobutyronitrile, 2,2-azobis-2,4-dimethylvaleronitrile, 4,4-azobis-4-cyanovaleric acid, 1,1-azobis-1-cyclohexanecarbonitrile, dimethyl-2,2-azobisisobutyrate, and 2,2-azobis-(2-aminopropane)dihydrochloride.

Examples of the photopolymerization initiator include (bis)acylphosphine oxides, water-soluble acylphosphine oxides, thioxanthones, ketals, α-diketones, coumarins, anthraquinones, benzoin alkyl ethers, and α-amino ketones.

Among (bis)acylphosphine oxides used as the above photopolymerization initiator, examples of the acylphosphine oxides include 2,4,6-trimethylbenzoyldiphenylphosphine oxide, 2,6-dimethoxybenzoyldiphenylphosphine oxide, 2,6-dichlorobenzoyldiphenylphosphine oxide, 2,4,6-trimethylbenzoylmethoxyphenylphosphine oxide, 2,4,6-trimethylbenzoylethoxyphenylphosphine oxide, 2,3,5,6-tetramethylbenzoyldiphenylphosphine oxide, benzoyl di-(2,6-dimethylphenyl)phosphonate, and salts thereof. Examples of the bisacylphosphine oxides include bis-(2,6-dichlorobenzoyl)phenylphosphine oxide, bis-(2,6-dichlorobenzoyl)-2,5-dimethylphenylphosphine oxide, bis-(2,6-dichlorobenzoyl)-4-propylphenylphosphine oxide, bis-(2,6-dichlorobenzoyl)-1-naphthylphosphine oxide, bis-(2,6-dimethoxybenzoyl)phenylphosphine oxide, bis-(2,6-dimethoxybenzoyl)-2,4,4-trimethylpentylphosphine oxide, bis-(2,6-dimethoxybenzoyl)-2,5-dimethylphenylphosphine oxide, bis-(2,4,6-trimethylbenzoyl)phenylphosphine oxide, (2,5,6-trimethylbenzoyl)-2,4,4-trimethylpentylphosphine oxide, and salts thereof.

Preferably, the water-soluble acylphosphine oxides used as the above photopolymerization initiator have alkali metal ions, alkaline earth metal ions, pyridinium ions, or ammonium ions in the acylphosphine oxide molecules. For instance, the water-soluble acylphosphine oxides can be synthesized by the method disclosed in EP 0009348 B1 or JP 57 (1982)-197289 A.

Specific examples of the above water-soluble acylphosphine oxides include sodium monomethylacetylphosphonate, sodium monomethyl(1-oxopropyl)phosphonate, sodium monomethylbenzoylphosphonate, sodium monomethyl(1-oxobutyl)phosphonate, sodium monomethyl(2-methyl-1-oxopropyl)phosphonate, sodium acetylphosphonate, sodium monomethylacetylphosphonate, sodium acetylmethylphosphonate, methyl-4-(hydroxymethoxyphosphinyl)-4-oxobutanoate sodium salt, methyl-4-oxophosphonobutanoate monosodium salt, acetylphenylphosphinate sodium salt, sodium (1-oxopropyl)pentylphosphinate, methyl-4-(hydroxypentylphosphinyl)-4-oxobutanoate sodium salt, sodium acetylpentylphosphinate, sodium acetylethylphosphinate, sodium methyl(1,1-dimethyl)methylphosphinate, sodium (1,1-diethoxyethyl)methylphosphinate, sodium (1,1-diethoxyethyl)methylphosphinate, methyl-4-(hydroxymethylphosphinyl)-4-oxobutanoate lithium salt, 4-(hydroxymethylphosphinyl)-4-oxobutanoic acid dilithium salt, methyl(2-methyl-1,3-dioxolan-2-yl)phosphinate sodium salt, methyl (2-methyl-1,3-thiazolidin-2-yl)phosphonite sodium salt, (2-methylperhydro-1,3-diazin-2-yl)phosphonite sodium salt, acetylphosphinate sodium salt, (1,1-diethoxyethyl)phosphonite sodium salt, (1,1-diethoxyethyl)methylphosphonite sodium salt, methyl(2-methyloxathiolane-2-yl)phosphinate sodium salt, methyl(2,4,5-trimethyl-1,3-dioxolan-2-yl)phosphinate sodium salt, methyl(1,1-propoxyethyl)phosphinate sodium salt, (1-methoxyvinyl)methylphosphinate sodium salt, (1-ethylthiovinyl)methylphosphinate sodium salt, methyl(2-methylperhydro-1,3-diazin-2-yl)phosphinate sodium salt, methyl(2-methylperhydro-1,3-thiazin-2-yl) phosphinate sodium salt, methyl(2-methyl-1,3-diazolidin-2-yl)phosphinate sodium salt, methyl(2-methyl-1,3-thiazolidin-2-yl)phosphinate sodium salt, (2,2-dicyano-1-methylethynyflphosphinate sodium salt, acetylmethylphosphinate oxime sodium salt, acetylmethylphosphinate-O-benzyloxime sodium salt, 1-[(N-ethoxyimino)ethyl]methylphosphinate sodium salt, methyl(1-phenyliminoethyl)phosphinate sodium salt, methyl(1-phenylhydrazone ethyl)phosphinate sodium salt, [1-(2,4-dinitrophenylhydrazono)ethyl]methylphosphinate sodium salt, acetylmethylphosphinate semicarbazone sodium salt, (1-cyano-1-hydroxyethyl)methylphosphinate sodium salt, (dimethoxymethyl)methyl phosphinate sodium salt, formylmethylphosphinate sodium salt, (1,1-dimethoxypropyl)methylphosphinate sodium salt, methyl(1-oxopropyl)phosphinate sodium salt, dodecylguanidine salt of (1,1-dimethoxypropyl)methylphosphinate, isopropylamine salt of (1,1-dimethoxypropyl)methylphosphinate, acetylmethylphosphinate thiosemicarbazone sodium salt, 1,3,5-tributyl-4-methylamino-1,2,4-triazolium (1,1-dimethoxyethyl)-methylphosphinate, 1-butyl-4-butylaminomethylamino-3,5-dipropyl-1,2,4-triazolium (1,1-dimethoxyethyl)-methylphosphinate, 2,4,6-trimethylbenzoylphenylphosphine oxide sodium salt, 2,4,6-trimethylbenzoylphenylphosphine oxide potassium salt, and ammonium salt of 2,4,6-trimethylbenzoylphenylphosphine oxide. Furthermore, examples thereof also include compounds described in JP 2000-159621 A.

Among these (bis)acylphosphine oxides and water-soluble acylphosphine oxides, particularly preferable ones are 2,4,6-trimethylbenzoyldiphenylphosphine oxide, 2,4,6-trimethylbenzoylmethoxyphenylphosphine oxide, bis(2,4,6-trimethylbenzoyl)phenylphosphine oxide, and 2,4,6-trimethylbenzoylphenylphosphine oxide sodium salt.

Examples of the thioxanthones or the quaternary ammonium salts of thioxanthones that are used as the above photopolymerization initiator include thioxanthone, 2-chlorothioxanthen-9-one,
2-hydroxy-3-(9-oxy-9H-thioxanthen-4-yloxy)-N,N,N-trimethyl-propaneaminium chloride,
2-hydroxy-3-(1-methyl-9-oxy-9H-thioxanthen-4-yloxy)-N,N,N-trimethyl-propaneaminium chloride,
2-hydroxy-3-(9-oxo-9H-thioxanthen-2-yloxy)-N,N,N-trimethyl-propaneaminium chloride,
2-hydroxy-3-(3,4-dimethyl-9-oxo-9H-thioxanthen-2-yloxy)-N,N,N-trimethyl-1-propaneaminium chloride,
2-hydroxy-3-(3,4-dimethyl-9H-thioxanthen-2-yloxy)-N,N,N-trimethyl-1-propaneaminium chloride, and
2-hydroxy-3-(1,3,4-trimethyl-9-oxo-9H-thioxanthen-2-yloxy)-N,N,N-trimethyl-1-propaneaminium chloride.

Among the thioxanthones or the quaternary ammonium salts of thioxanthones, a particularly preferable thioxanthone is 2-chlorothioxanthen-9-one, and a particularly preferable quaternary ammonium salt of thioxanthone is 2-hydroxy-3-(3,4-dimethyl-9H-thioxanthen-2-yloxy)-N,N,N-trimethyl-1-propaneaminium chloride.

Examples of ketals used as the above photopolymerization initiator include benzyl dimethyl ketal and benzyl diethyl ketal.

Examples of the α-diketones used as the above photopolymerization initiator include diacetyl, dibenzyl, camphorquinone, 2,3-pentadione, 2,3-octadione, 9,10-phenanthrenequinone, 4,4'-oxybenzyl, and acenaphthenequinone. Among these, camphorquinone is preferred.

Examples of the coumarins that are used as the above photopolymerization initiator include compounds described in JP 09(1997)-003109 A and JP 10(1998)-245525 A, such as 3,3'-carbonyl bis(7-diethylamino)coumarin, 3-(4-methoxybenzoyl)coumarin-5,7-dimethoxycoumarin, 3-thienoyl coumarin, 3-benzoyl-5,7-dimethoxycoumarin, 3-benzoyl-7-methoxycoumarin, 3-benzoyl-6-methoxycoumarin, 3-benzoyl-8-methoxycoumarin, 3-benzoylcoumarin, 7-methoxy-3-(p-nitrobenzoyl)coumarin, 3-(p-nitrobenzoyl)coumarin, 3,5-carbonylbis(7-methoxycoumarin), 3-benzoyl-6-bromocoumarin, 3,3'-carbonylbiscoumarin, 3-benzoyl-7-dimethylaminocoumarin, 3-benzoylbenzoyl)coumarin, 3-carboxycoumarin, 3-carboxy-7-methoxycoumarin, 3-ethoxycarbonyl-6-methoxycoumarin, 3-ethoxycarbonyl-8-methoxycoumarin, 3-acetylbenzo[f]coumarin, 7-methoxy-3-(p-nitrobenzoyl)coumarin, 3-(p-nitrobenzoyl)coumarin, 3-benzoyl-6-nitrocoumarin, 3-benzoyl-7-diethylaminocoumarin, 7-dimethylamino-3-(4-methoxybenzoyl)coumarin, 7-diethylamino-3-(4-methoxybenzoyl)coumarin, 7-diethylamino-3-(4-diethylamino)coumarin, 7-methoxy-3-(4-methoxybenzoyl)coumarin, 3-(4-nitrobenzoyl)benzo[f]coumarin, 3-(4-ethoxycinnamoyl)-7-methoxycoumarin, 3-(4-dimethylaminocinnamoyl) coumarin, 3-(4-diphenylaminocinnamoyl)coumarin, 3-[(3-dimethylbenzothiazole-2-ylidene)acetyl]coumarin, 3-[(1-methylnaphtho[1,2-d]thiazol-2-ylidene)acetyl]coumarin, 3,3'-carbonylbis(6-methoxycoumarin), 3,3'-carbonylbis(7-acetoxycoumarin), 3,3'-carbonylbis(7-dimethylaminocoumarin), 3-(2-benzothiazoyl)-7-(diethylamino)coumarin, 3-(2-benzothiazoyl)-7-(dibutylamino)coumarin, 3-(2-benzoimidazoyl)-7-(diethylamino)coumarin, 3-(2-benzothiazoyl)-7-(dioctylamino)coumarin, 3-acetyl-7-(dimethylamino)coumarin, 3,3'-carbonylbis(7-dibutylaminocoumarin), 3,3'-carbonyl-7-diethylaminocoumarin-7'-bis(butoxyethyl) aminocoumarin, 10-[3-[4-(dimethylamino)phenyl]-1-oxo-2-propenyl]-2,3,6,7-1,1,7,7-tetramethyl 1H,5H,11H-[1]benzopyrano[6,7,8-ij]quinolidin-11-one, and 10-(2-benzothiazoyl)-2,3,6,7-tetrahydro-1,1,7,7-tetramethyl 1H,5H,11H-[1]benzopyrano[6,7,8-ij]quinolidin-11-one.

Among the above-mentioned coumarin compounds, 3,3'-carbonyl bis(7-diethylaminocoumarin) and 3,3'-carbonylbis (7-dibutylaminocoumarin) are preferred.

Examples of the anthraquinones used as the above photopolymerization initiator include anthraquinone, 1-chloroanthraquinone, 2-chloroanthraquinone, 1-bromoanthraquinone, 1,2-benzanthraquinone, 1-methylanthraquinone, 2-ethylanthraquinone, and 1-hydroxyanthraquinone.

Examples of the benzoin alkyl ethers used as the above photopolymerization initiator include benzoin methyl ether, benzoin ethyl ether, benzoin isopropyl ether, and benzoin isobutyl ether.

Examples of the α-aminoketones used as the above photopolymerization initiator include 2-methyl-1-[4-(methylthio) phenyl]-2-morpholinopropan-1-one.

It is preferable to use, among these photopolymerization initiators, at least one selected from the group consisting of (bis)acylphosphine oxides, α-diketones, and coumarins, which are widely used in dental curable compositions.

As the chemical polymerization initiators, organic peroxides are preferably used. The organic peroxides used as the above chemical polymerization initiator are not particularly limited and any known one can be used. Specific examples thereof include organic peroxides described as examples of the above thermal polymerization initiator.

Among these organic peroxides, diacyl peroxides are used preferably from the viewpoint of an overall balance of safety, storage stability, and radical production ability, and among these, benzoyl peroxide is used more preferably.

The content of the polymerization initiator used for the curable composition to fabricate the dental mill blank is not particularly limited. However, from the viewpoint of, for example, curability, etc. of the resultant composition, it is preferable that 0.001 to 30 parts by weight of the polymerization initiator be contained per 100 parts by weight of the polymerizable monomer (A). When the content of the polymerization initiator is 0.001 parts by weight or more, polymerization proceeds sufficiently and thereby the composition is free from a decrease in the mechanical strength. Therefore, the content is more preferably 0.05 parts by weight or more, and further preferably 0.10 parts by weight or more. On the other hand, when the content of the polymerization initiator is 30 parts by weight or less, even in the case where the polymerization initiator itself has low polymerization performance, sufficient mechanical strength can be obtained and furthermore the composition is free from precipitation. Therefore, the content is more preferably 20 parts by weight or less, and further preferably 15 parts by weight or less.

The curable composition used to fabricate the dental mill blank of the present invention may contain a polymerization accelerator to facilitate curing through polymerization. The polymerization accelerator can be selected from polymerization accelerators commonly used in the industrial field. Among them, polymerization accelerators used for dental applications are used preferably. Polymerization accelerators are used alone, or two or more of them are used in appropriate combination.

Examples of the polymerization accelerator include amines, sulfinic acids and salts thereof, borate compounds, barbituric acid derivatives, triazine compounds, copper compounds, tin compounds, vanadium compounds, halogen compounds, aldehydes, thiol compounds, sulfites, bisulfites, and thiourea compounds.

Amines used as the polymerization accelerator can be divided into aliphatic amines and aromatic amines. Examples of aliphatic amines include: primary aliphatic amines such as n-butylamine, n-hexylamine, and n-octylamine; secondary aliphatic amines such as diisopropylamine, dibutylamine, and N-methylethanolamine; and tertiary aliphatic amines such as N-methyldiethanolamine, N-ethyldiethanolamine, N-n-butyldiethanolamine, N-lauryldiethanolamine, 2-(dimethylamino)ethyl methacrylate, N-methyldiethanolamine dimethacrylate, N-ethyldiethanolamine dimethacrylate, triethanolamine monomethacrylate, triethanolamine dimethacrylate, triethanolamine trimethacrylate, triethanolamine, trimethylamine, triethylamine, and tributylamine. Among these, tertiary aliphatic amines are preferable from the viewpoints of curability and storage stability of the composition, and particularly, N-methyldiethanolamine and triethanolamine are used more preferably.

Examples of aromatic amines include N,N-bis(2-hydroxyethyl)-3,5-dimethylaniline, N,N-di(2-hydroxyethyl)-p-toluidine, N,N-bis(2-hydroxyethyl)-3,4-dimethylaniline, N,N-bis (2-hydroxyethyl)-4-ethylaniline, N,N-bis(2-hydroxyethyl)-4-isopropylaniline, N,N-bis(2-hydroxyethyl)-4-t-butylaniline, N,N-bis(2-hydroxyethyl)-3,5-diisopropylaniline, N,N-bis(2-hydroxyethyl)-3,5-di-t-butylaniline, N,N-dimethylaniline, N,N-dimethyl-p-toluidine, N,N-dimethyl-m-toluidine, N,N-diethyl-p-toluidine, N,N-dimethyl-3,5-dimethylaniline, N,N-dimethyl-3,4-dimethylaniline, N,N-dimethyl-4-ethylaniline, N,N-dimethyl-4-isopropylaniline, N,N-dimethyl-4-t-butylaniline, N,N-dimethyl-3,5-di-t-butylaniline, 4-N,N-dimethylaminobenzoic acid ethyl ester, 4-N,N-dimethylaminobenzoic acid methyl ester, N,N-dimethylaminobenzoic acid n-butoxyethyl ester, 4-N,N-dimethylaminobenzoic acid 2-(methacryloyloxy)ethyl ester, 4-N,N-dimethylaminobenzophenone, and butyl 4-dimethylaminobenzoate. Among these, at least one selected from the group consisting of N,N-di(2-hydroxyethyl)-p-toluidine, 4-N,N-dimethylaminobenzoic acid ethyl ester, N,N-dimethylaminobenzoic acid n-butoxyethyl ester, and 4-N,N-dimethylaminobenzophenone is used preferably from the viewpoint of being capable of imparting excellent curability to the composition.

Examples of the sulfinic acid or salt thereof used as the polymerization accelerator include p-toluenesulfinic acid, sodium p-toluenesulfinate, potassium p-toluenesulfinate, lithium p-toluenesulfinate, calcium p-toluenesulfinate, benzenesulfinic acid, sodium benzenesulfinate, potassium benzenesulfinate, lithium benzenesulfinate, calcium benzenesulfinate, 2,4,6-trimethylbenzenesulfinic acid, sodium 2,4,6-trimethylbenzenesulfinate, potassium 2,4,6-trimethylbenzenesulfinate, lithium 2,4,6-trimethylbenzenesulfinate, calcium 2,4,6-trimethylbenzenesulfinate, 2,4,6-triethylbenzenesulfinic acid, sodium 2,4,6-triethylbenzenesulfinate, potassium 2,4,6-triethylbenzenesulfinate, lithium 2,4,6-triethylbenzenesulfinate, calcium 2,4,6-triethylbenzenesulfinate, 2,4,6-triisopropylbenzenesulfinic acid, sodium 2,4,6-triisopropylbenzenesulfinate, potassium 2,4,6-triisopropylbenzenesulfinate, lithium 2,4,6-triisopropylbenzenesulfinate, and calcium 2,4,6-triisopropylbenzenesulfinate. Sodium benzenesulfinate, sodium p-toluenesulfinate, and sodium 2,4,6-triisopropylbenzenesulfinate are preferred.

The borate compound used as the polymerization accelerator is preferably an arylborate compound. Specific examples of arylborate compounds that are used preferably include, as a borate compound having one aryl group in one molecule, sodium salt, lithium salt, potassium salt, magnesium salt, tetrabutylammonium salt, tetramethylammonium salt, tetraethylammonium salt, methylpyridinium salt, ethylpyridinium salt, butylpyridinium salt, methylquinolinium salt, ethylquinolinium salt, and butylquinolinium salt of trialkylphenylboron, trialkyl(p-chlorophenyl)boron, trialkyl(p-fluorophenyl)boron, trialkyl(3,5-bistrifluoromethyl)phenylboron, trialkyl[3,5-bis(1,1,1,3,3,3-hexafluoro-2-methoxy-2-propyl)phenyl]boron, trialkyl(p-nitrophenyl)boron, trialkyl (m-nitrophenyl)boron, trialkyl(p-butylphenyl)boron, trialkyl (m-butylphenyl)boron, trialkyl(p-butyloxyphenyl)boron, trialkyl(m-butyloxyphenyl)boron, trialkyl(p-octyloxyphenyl)boron, and trialkyl(m-octyloxyphenyl)boron (each alkyl group is at least one selected from the group consisting of, for example, an n-butyl group, an n-octyl group, and an n-dodecyl group).

Examples of the borate compound having two aryl groups in one molecule include sodium salt, lithium salt, potassium salt, magnesium salt, tetrabutylammonium salt, tetramethylammonium salt, tetraethylammonium salt, methylpyridinium salt, ethylpyridinium salt, butylpyridinium salt, methylquinolinium salt, ethylquinolinium salt, and butylquinolinium salt of dialkyldiphenylboron, dialkyldi(p-chlorophenyl)boron, dialkyldi(p-fluorophenyl)boron, dialkyldi(3,5-bistrifluoromethyl)phenylboron, dialkyldi[3,5-bis(1,1,1,3,3,3-hexafluoro-2-methoxy-2-propyl)phenyl]boron, dialkyldi(p-nitrophenyl)boron, dialkyldi(m-nitrophenyl)boron, dialkyldi(p-butylphenyl)boron, dialkyldi(m-butylphenyl)boron, dialkyldi(p-butyloxyphenyl)boron, dialkyldi(m-butyloxyphenyl)boron, dialkyldi(p-octyloxyphenyl)boron, and dialkyldi(m-octyloxyphenyl)boron (each alkyl group is at least one selected from the group consisting of, for example, an n-butyl group, an n-octyl group, and an n-dodecyl group).

Examples of the borate compound having three aryl groups in one molecule include sodium salt, lithium salt, potassium salt, magnesium salt, tetrabutylammonium salt, tetramethylammonium salt, tetraethylammonium salt, methylpyridinium salt, ethylpyridinium salt, butylpyridinium salt, methylquinolinium salt, ethylquinolinium salt, and butylquinolinium salt of monoalkyltriphenylboron, monoalkyltri(p-chlorophenyl)boron, monoalkyltri(p-fluorophenyl)boron, monoalkyltri(3,5-bistrifluoromethyl)phenylboron, monoalkyltri[3,5-bis(1,1,1,3,3,3-hexafluoro-2-methoxy-2-propyl)phenyl]boron, monoalkyltri(p-nitrophenyl)boron, monoalkyltri(m-nitrophenyl)boron, monoalkyltri(p-butylphenyl)boron, monoalkyltri(m-butylphenyl)boron, monoalkyltri(p-butyloxyphenyl)boron, monoalkyltri(m-butyloxyphenyl)boron, monoalkyltri(p-octyloxyphenyl)boron, and monoalkyltri(m-octyloxyphenyl) boron (each alkyl group is one selected from, for example, an n-butyl group, an n-octyl group, and an n-dodecyl group).

Furthermore, examples of the borate compound having four aryl groups in one molecule include sodium salt, lithium salt, potassium salt, magnesium salt, tetrabutylammonium salt, tetramethylammonium salt, tetraethylammonium salt, methylpyridinium salt, ethylpyridinium salt, butylpyridinium salt, methylquinolinium salt, ethylquinolinium salt, and butylquinolinium salt of tetraphenylboron, tetrakis(p-chlorophenyl)boron, tetrakis(p-fluorophenyl)boron, tetrakis(3,5-bistrifluoromethyl)phenylboron, tetrakis[3,5-bis(1,1,1,3,3,3-hexafluoro-2-methoxy-2-propyl)phenyl]boron, tetrakis(p-nitrophenyl)boron, tetrakis(m-nitrophenyl)boron, tetrakis(p-butylphenyl)boron, tetrakis(m-butylphenyl)boron, tetrakis (p-butyloxyphenyl)boron, tetrakis(m-butyloxyphenyl) boron, tetrakis(p-octyloxyphenyl)boron, tetrakis(m-octyloxyphenyl)boron, (p-fluorophenyl)triphenylboron, (3,5-bistrifluoromethyl)phenyltriphenylboron, (p-nitrophenyl)triphenylboron, (m-butyloxyphenyl)triphenylboron, (p-butyloxyphenyl)triphenylboron, (m-octyloxyphenyl) triphenylboron, and (p-octyloxyphenyl)triphenylboron.

More preferably, from the viewpoint of storage stability, among these arylborate compounds, a borate compound having three or four aryl groups in one molecule is used. Furthermore, one of these arylborate compounds can be used or two or more of them can be used in mixture.

Examples of the barbituric acid derivative used as the polymerization accelerator include barbituric acid, 1,3-dimethylbarbituric acid, 1,3-diphenylbarbituric acid, 1,5-dimethylbarbituric acid, 5-butylbarbituric acid, 5-ethylbarbituric acid, 5-isopropylbarbituric acid, 5-cyclohexylbarbituric acid, 1,3, 5-trimethylbarbituric acid, 1,3-dimethyl-5-ethylbarbituric acid, 1,3-dimethyl-n-butylbarbituric acid, 1,3-dimethyl-5- isobutylbarbituric acid, 1,3-dimethylbarbituric acid, 1,3-dimethyl-5-cyclopentylbarbituric acid, 1,3-dimethyl-5-cyclohexylbarbituric acid, 1,3-dimethyl-5-phenylbarbituric acid, 1-cyclohexyl-1-ethylbarbituric acid, 1-benzyl-5-phenylbarbituric acid, 5-methylbarbituric acid, 5-propylbarbituric acid, 1,5-diethylbarbituric acid, 1-ethyl-5-methylbarbituric acid, 1-ethyl-5-isobutylbarbituric acid, 1,3-diethyl-5-butylbarbituric acid, 1-cyclohexyl-5-methylbarbituric acid, 1-cyclohexyl-5-ethylbarbituric acid, 1-cyclohexyl-5-octylbarbituric acid, 1-cyclohexyl-5-hexylbarbituric acid, 5-butyl-1-cyclohexylbarbituric acid, 1-benzyl-5-phenylbarbituric acid, and thiobarbituric acids, as well as salts thereof (alkali metals or alkaline earth metals are preferable). Examples of the salts of these barbituric acids include sodium 5-butylbarbiturate, sodium 1,3,5-trimethylbarbiturate, and sodium 1-cyclohexyl-5-ethylbarbiturate.

Examples of preferable barbituric acid derivatives include 5-butylbarbituric acid, 1,3,5-trimethylbarbituric acid, 1-cyclohexyl-5-ethylbarbituric acid, 1-benzyl-5-phenylbarbituric acid, and sodium salts of these barbituric acids.

Examples of the triazine compound used as the polymerization accelerator include 2,4,6-tris(trichloromethyl)-s-triazine, 2,4,6-tris(tribromomethyl)-s-triazine, 2-methyl-4,6-bis(trichloromethyl)-s-triazine, 2-methyl-4,6-bis(tribromomethyl)-s-triazine, 2-phenyl-4,6-bis(trichloromethyl)-s-triazine, 2-(p-methoxyphenyl)-4,6-bis(trichloromethyl)-s-triazine, 2-(p-methylthiophenyl)-4,6-bis(trichloromethyl)-s-triazine, 2-(p-chlorophenyl)-4,6-bis(trichloromethyl)-s-triazine, 2-(2,4-dichlorophenyl)-4,6-bis(trichloromethyl)-s-triazine, 2-(p-bromophenyl)-4,6-bis(trichloromethyl)-s-triazine, 2-(p-tolyl)-4,6-bis(trichloromethyl)-s-triazine, 2-n-propyl-4,6-bis(trichloromethyl)-s-triazine, 2-($\alpha,\alpha,\beta$-trichloroethyl)-4,6-bis(trichloromethyl)-s-triazine, 2-styryl-4,6-bis(trichloromethyl)-s-triazine, 2-[2-(p-methoxyphenyl)ethenyl]-4,6-bis(trichloromethyl)-s-triazine, 2-[2-(o-methoxyphenyl)ethenyl]-4,6-bis(trichloromethyl)-s-triazine, 2-[2-(p-butoxyphenyl)ethenyl]-4,6-bis(trichloromethyl)-s-triazine, 2-[2-(3,4-dimethoxyphenyl)ethenyl]-4,6-bis(trichloromethyl)-s-triazine, 2-[2-(3,4,5-trimethoxyphenyl)ethenyl]-4,6-bis(trichloromethyl)-s-triazine, 2-(1-naphthyl)-4,6-bis(trichloromethyl)-s-triazine, 2-(4-biphenylyl)-4,6-bis(trichloromethyl)-s-triazine, 2-[2-{N,N-bis(2-hydroxyethyl)amino}ethoxy]-4,6-bis(trichloromethyl)-s-triazine, 2-[2-{N-hydroxyethyl-N-ethylamino}ethoxy]-4,6-bis(trichloromethyl)-s-triazine, 2-[2-{N-hydroxyethyl-N-methylamino}ethoxy]-4,6-bis(trichloromethyl)-s-triazine, and 2-[2-{N,N-diallylamino}ethoxy]-4,6-bis(trichloromethyl)-s-triazine.

Preferable ones among the triazine compounds described above as examples are 2,4,6-tris(trichloromethyl)-s-triazine in terms of polymerization activity and 2-phenyl-4,6-bis(trichloromethyl)-s-triazine, 2-(p-chlorophenyl)-4,6-bis(trichloromethyl)-s-triazine, and 2-(4-biphenylyl)-4,6-bis(trichloromethyl)-s-triazine in terms of storage stability. One of the above-mentioned triazine compounds may be used, or two or more of them may be used in mixture.

Examples of the copper compound used preferably as the polymerization accelerator include copper acetylacetonate, copper (II) acetate, copper oleate, copper (II) chloride, and copper (II) bromide.

Examples of the tin compound used as the polymerization accelerator include di-n-butyltin dimalate, di-n-octyltin dimalate, di-n-octyltin dilaurate, and di-n-butyltin dilaurate. Particularly preferable tin compounds are di-n-octyltin dilaurate and di-n-butyltin dilaurate.

The vanadium compound used as the polymerization accelerator is preferably one of tetravalent and/or pentavalent vanadium compounds. Examples of the tetravalent and/or pentavalent vanadium compounds include compounds described in JP 2003-96122 A such as divanadium (IV) tetroxide, vanadyl (IV) acetylacetonate, vanadyl (IV) oxalate, vanadyl (IV) sulfate, oxobis(1-phenyl-1,3-butanedionate)vanadium (IV), bis(maltolato)oxovanadium (IV), vanadium (V) pentoxide, sodium metavanadate (V), and ammonium metavanadate (V).

Examples of the halogen compound used as the polymerization accelerator include dilauryldimethylammoniumchloride, lauryldimethylbenzylammoniumchloride, benzyltrimethylammoniumchloride, tetramethylammoniumchloride, benzyldimethylcetylammoniumchloride, and dilauryldimethylammoniumbromide.

Examples of aldehydes used as the polymerization accelerator include terephthalaldehyde and a benzaldehyde derivative. Examples of the benzaldehyde derivative include dimethylaminobenzaldeyde, p-methyloxybenzaldehyde, p-ethyloxybenzaldehyde, and p-n-octyloxybenzaldehyde. Among these, from the viewpoint of curability, p-n-octyloxybenzaldehyde is used preferably.

Examples of the thiol compound used as the polymerization accelerator include 3-mercaptopropyltrimethoxysilane, 2-mercaptobenzooxazol, decanethiol, and thiobenzoic acid.

Examples of sulfite used as the polymerization accelerator include sodium sulfite, potassium sulfite, calcium sulfite, and ammonium sulfite.

Examples of bisulfite used as the polymerization accelerator include sodium bisulfite and potassium bisulfite.

Examples of the thiourea compound used as the polymerization accelerator include 1-(2-pyridyl)-2-thiourea, thiourea, methylthiourea, ethylthiourea, N,N'-dimethylthiourea, N,N'-diethylthiourea, N,N'-di-n-propylthiourea, N,N'-dicyclohexylthiourea, trimethylthiourea, triethylthiourea, tri-n-propylthiourea, tricyclohexylthiourea, tetramethylthiourea, tetraethylthiourea, tetra-n-propylthiourea, and tetracyclohexylthiourea.

The content of a polymerization accelerator used for the curable composition to fabricate the dental mill blank is not particularly limited. However, from the viewpoints of, for example, curability of the resultant composition, it is preferable that 0.001 to 30 parts by weight of polymerization accelerator be contained per 100 parts by weight of the polymerizable monomer (A). When the content of the polymerization accelerator is 0.001 parts by weight or more, polymerization proceeds sufficiently and thereby the composition is free from a decrease in the mechanical strength. Therefore, the content is more preferably 0.05 parts by weight or more, and further preferably 0.1 parts by weight or more. On the other hand, when the content of the polymerization accelerator is 30 parts by weight or less, even in the case where the polymerization initiator itself has low polymerization performance, sufficient mechanical strength can be obtained and furthermore the composition is free from precipitation. Therefore, the content is more preferably 20 parts by weight or less.

To the curable composition, a pH adjuster, an ultraviolet absorber, an antioxidant, a polymerization inhibitor, a colorant, an antibacterial agent, an X-ray contrast agent, a thickening agent, a fluorescent agent, or the like can further be added in accordance with the intended use.

For example, when the cured surface is expected to have a fluorine ion sustained-release property, a fluorine ion sustained-releasable filler, such as fluoroaluminosilicate glass, calcium fluoride, sodium fluoride, or sodium monofluorophosphate also can be added.

When it is expected to have an antibacterial property, for example, a surfactant having an antibacterial activity, such as cetylpyridinium chloride, or a photocatalytic titanium oxide can be added.

The dental mill blank of the present invention can be obtained, for example, by filling the curable composition containing the above-mentioned components in a mold to polymerize/cure the composition by thermal polymerization and/or photopolymerization and/or chemical polymerization into a block shape. Curing through polymerization under pressure can increase the rate of polymerization and further increase the mechanical strength. Furthermore, heat treatment after the curing through polymerization can relax the stress strain generated in the block and suppress the cracking of a dental prosthesis during machining or clinical use thereof.

Machining of the dental mill blank of the present invention using a CAD/CAM system makes it possible to provide an aesthetic dental prosthesis having high mechanical/physical properties and excellent gloss retention.

EXAMPLES

The present invention will be described in more detail below by the following examples, without intending to limit the scope of the present invention to these examples. The materials, test methods, etc. used in the examples are shown below.

Preparation Example 1

Preparation of Polymerizable Monomer A 1 part by weight of benzoyl peroxide as a polymerization initiator was dissolved in 20 parts by weight of 2,2-bis[4-(3-methacryloyloxy-2-hydroxypropoxy)phenyl]propane, 50 parts by weight of 2,2-bis[4-methacryloyloxypolyethoxyphenyl]propane, and 30 parts by weight of triethylene glycol dimethacrylate to prepare a polymerizable monomer A. The polymerizable monomer A was degassed and then photopolymerized to obtain a cured product. Then, the cured product thus obtained was formed into a rectangular parallelepiped of 5 mm×10 mm×20 mm, and the refractive index thereof was measured according to the following method. The refractive index of the polymerizable monomer A after polymerization was 1.55.

[Refractive Index]

The refractive index was measured with an Abbe's refractometer by the immersion method, in which a sodium D-line was used as a light source, and diiodomethane in which sulfur is dissolved, 1-bromonaphthalene, methyl salicylate, dimethylformamide, 1-pentanol, or the like was used as a liquid.

Preparation Example 2

Preparation of Spherical Filler B-1

100 g of commercially available silica-zirconia spherical filler (manufactured by Sukgyung AT Co., Ltd., average primary particle size of 203 nm) was dispersed in 500 mL of ethanol, and 6 g of γ-methacryloxypropyltrimethoxysilane and 3 g of water were added to the dispersion, which was stirred at room temperature for 2 hours. Then, the solvent was distilled off under reduced pressure, followed by drying at 90° C. for 3 hours. Thus, surface treatment was performed, and a spherical filler B-1 was obtained. The refractive index thereof measured by the above method was 1.55.

Preparation Example 3

Preparation of Spherical Filler B-2

100 g of commercially available silica (manufactured by Sakai Chemical Industry Co., Ltd., average primary particle size of 100 nm) was surface-treated using 10 g of γ-methacryloxypropyltrimethoxysilane and 5 g of water in the same manner as in Preparation Example 2. Thus, a spherical filler B-2 was obtained. The refractive index thereof measured by the above method was 1.45.

Preparation Example 4

Preparation of Spherical Filler B-3

100 g of commercially available silica (manufactured by Sakai Chemical Industry Co., Ltd., average primary particle size of 700 nm) was surface-treated using 4 g of γ-methacryloxypropyltrimethoxysilane and 2 g of water in the same manner as in Preparation Example 2. Thus, a spherical filler B-3 was obtained. The refractive index thereof measured by the above method was 1.45.

Preparation Example 5

Preparation of Inorganic Ultrafine Particle Aggregates C-1

A commercially available silica sol (manufactured by Nissan Chemical Industries, Ltd., average primary particle size of 10 nm) was spray-dried with a spray dryer (B-290 manufactured by Buchi) to obtain an aggregated powder. This aggregated powder was composed of spherical particles having an average particle size of 5 μm. This aggregated powder was calcined at 950° C. for 1 hour, and then 100 g of the powder was surface-treated using 20 g of γ-methacryloxypropyltrimethoxysilane and 10 g of water in the same manner as in Preparation Example 2. Thus, inorganic ultrafine particle aggregates C-1 were obtained. The refractive index thereof measured by the above method was 1.45.

Preparation Example 6

Preparation of Inorganic Ultrafine Particle Aggregates C-2

A commercially available silica sol (manufactured by Nissan Chemical Industries, Ltd., average primary particle size of 10 nm) was diluted with water by 5 times to prepare a diluted sol. This diluted sol was spray-dried with a spray dryer (B-290 manufactured by Buchi) to obtain an aggregated powder. This aggregated powder was composed of spherical particles having an average particle size of 1 μm. This aggregated powder was calcined at 950° C. for 1 hour, and then 100 g of the powder was surface-treated using 20 g of γ-methacryloxypropyltrimethoxysilane and 10 g of water in the same manner as in Preparation Example 2. Thus, inorganic ultrafine particle aggregates C-2 were obtained. The refractive index thereof measured by the above method was 1.45.

Preparation Example 7

Preparation of Ground-type Filler D 100 g of a commercially available Ba glass (manufactured by Schott, average primary particle size of 2 μm) was surface-treated using 3 g of γ-methacryloxypropyltrimethoxysilane and 1.5 g of water in the same manner as in Preparation Example 2. Thus, a ground-type filler D was obtained. The refractive index thereof measured by the above method was 1.55.

Preparation Example 8

Preparation of Ultrafine Particle Inorganic Filler E 100 g of commercially available ultrafine silica particles (manufactured by Japan Aerosil Co., Ltd., average primary particle size of 16 nm) were surface-treated using 30 g of γ-methacryloxypropyltrimethoxysilane and 15 g of water in the same manner as in Preparation Example 2. Thus, an ultrafine particle inorganic filler E was obtained. The refractive index thereof measured by the above method was 1.45.

Preparation Example 9

Preparation of Ground-type Filler F 100 g of a commercially available Ba glass (manufactured by Schott, average primary particle size of 0.7 μm) was surface-treated using 4 g of γ-methacryloxypropyltrimethoxysilane and 2.0 g of water in the same manner as in Preparation Example 2. Thus, a ground-type filler F was obtained. The refractive index thereof measured by the above method was 1.55.

Preparation Example 10

Preparation of Ground-type Filler G

A commercially available quartz powder (manufactured by Maruwa Quartz Co., Ltd.) was ground in a ball mill for 24 hours to obtain a powder having an average primary particle size of 2.0 μm. This powder was subjected to grinding processing 5 times with Nano Jetmizer (NJ-100, manufactured by Aishin Nano Technologies Co., Ltd.) at a material feed pressure of 1.3 MPa and a grinding pressure of 1.3 MPa as the grinding pressure conditions and at a rate of 1 Kg per hour as the processing condition. Thus, a quartz powder having an average primary particle size of 0.7 μm was obtained. 100 g of the quartz powder having an average primary particle size of 0.7 μm was surface-treated using 4 g of γ-methacryloxypropyltrimethoxysilane and 2.0 g of water in the same manner as in Preparation Example 2. Thus, a ground-type filler G was obtained. The refractive index thereof measured by the above method was 1.45.

Examples 1 to 9 and Comparative Examples 1 to 5

The polymerizable monomer A, the spherical fillers B-1, B-2 and B-3, the inorganic ultrafine particle aggregates C-1 and C-2, the ground-type filler D, the ultrafine particle inorganic filler E, the ground-type filler F, and the ground-type filler G were mixed at ratios shown in Table 1 to obtain curable compositions. Each of the curable compositions was filled in a block-shaped mold of 20 mm×30 mm×10 mm, and cured through polymerization by hot pressing at 100° C. and a pressure of 10 MPa for 10 minutes using a pressing machine. Thus, block-shaped cured products of Examples 1 to 9 and Comparative Examples 1 to 3 were obtained.

The properties of the dental mill blanks thus obtained were examined according to the following test examples 1 to 4. Table 1 shows the results thereof.

Test Example 1

Measurement of Flexural Strength

From the dental mill blank thus produced, a specimen (2 mm×2 mm×30 mm) was cut out with a diamond cutter. The specimen was immersed in water at 37° C. for 24 hours. Then, the specimen was mounted on a universal testing machine (manufactured by Instron), and its three-point flexural strength was measured with a span of 20 mm at a crosshead speed of 1 mm/min. A flexural strength of 80 MPa or more is considered preferable.

Test Example 2

Evaluation of Gloss Retention

From the dental mill blank thus produced, a resin plate (2 mm thick, 30 mm long, and 20 mm wide) was cut out with a diamond cutter. The surface of the resin plate was polished with a #1500 waterproof abrasive paper. Then, this polished surface was buffed with a dental polishing kit (EWL 80, manufactured by KAVO) at 3000 rpm for 20 seconds. Thus, a specimen was obtained. As a polishing material, Porceny Hydron (manufactured by Tokyo Shizaisha) was used. The gloss level (G1) of the specimen before an abrasion test was measured with a glossmeter (VG-107, manufactured by Nippon Denshoku Industries Co., Ltd.) and shown as a ratio to the specular gloss of 100%. The measurement was performed at an angle of 60 degrees. The specimen was subjected to an abrasion test using a toothbrush abrasion tester (manufactured by Daiei Kagaku Seiki MFG.). The abrasion test was performed for 40000 abrasion cycles under a load of 250 g using a commercially available slurry of 60 parts by weight of dentifrice and 40 parts by weight of distilled water and a commercially available toothbrush. The gloss level (G2) of the surface of the specimen after the abrasion test was shown in the same manner as the gloss level before the abrasion test. The gloss retention was represented as (G2)×100/(G1) % based on the gloss levels of the surface of the specimen before and after the abrasion test. A gloss retention of 70% or more is considered preferable.

Test Example 3

Measurement of Transparency

From the dental mill blank thus produced, a disk-shaped specimen (20 mm diameter×1.0 mm) was cut out with a diamond cutter. The lightness (Lw) of the specimen on a standard white plate placed behind the specimen and the lightness (Lb) of the same specimen on a standard black plate placed behind the specimen were measured using a spectrophotometer (CM-3610d manufactured by Minolta Co., Ltd.) equipped with an illuminant C and a 2° observer, and the difference between the lightness (Lw) and the lightness (Lb) (ΔL=Lw−Lb) was calculated to be used as a measure of transparency. A higher value of ΔL means a higher level of the transparency of the specimen.

Test Example 4

Measurement of Total Light Transmittance and Haze

From the dental mill blank thus produced, a specimen (a diameter of 30 mm×a thickness of 0.25 mm) was cut out with a diamond cutter. The total light transmittance and haze of the specimen were measured with a haze meter (NDH-5000, manufactured by Nippon Denshoku Industries Co., Ltd.). The haze can be calculated by the following equation:

Haze=Diffuse transmittance/Total light transmittance× 100(%).

Higher values of the total light transmittance and the haze mean a higher level of light diffusibility of the specimen.

size of the former was smaller than that of the latter. However, due to the irregular shape of the ground-type filler, the gloss retention was lower than that of Example 5. In Comparative Example 5, the gloss retention was low, as in Comparative Example 4. In addition, since the refractive index of the filler was as low as 1.45, the transparency of the resulting curable composition was low.

TABLE 1

|  |  |  | Ex. 1 | Ex. 2 | Ex. 3 | Ex. 4 | Ex. 5 | Ex. 6 | Ex. 7 | Ex. 8 | Ex. 9 |
|---|---|---|---|---|---|---|---|---|---|---|---|
| Compositions | Polymerizable monomer A |  | 100 | 100 | 100 | 100 | 100 | 100 | 100 | 100 | 100 |
|  | Spherical filler | B-1 | 150 | 100 | 800 |  |  | 150 | 150 | 150 | 150 |
|  |  | B-2 |  |  |  | 150 |  |  |  |  |  |
|  |  | B-3 |  |  |  |  | 150 |  |  |  |  |
|  | Inorganic ultrafine particle aggregates | C-1 |  |  |  |  |  | 2 | 10 | 25 |  |
|  |  | C-2 |  |  |  |  |  |  |  |  | 10 |
| Properties | Flexural strength (MPa) |  | 142 | 119 | 171 | 147 | 136 | 144 | 149 | 153 | 152 |
|  | Gloss retention (%) |  | 88 | 85 | 92 | 93 | 84 | 85 | 83 | 80 | 87 |
|  | Transparency (ΔL) |  | 35 | 34 | 36 | 23 | 15 | 32 | 30 | 27 | 28 |
|  | Haze (%) |  | 55 | 58 | 53 | 78 | 82 | 93 | 95 | 97 | 96 |
|  | Total light transmittance (%) |  | 88 | 87 | 89 | 67 | 55 | 87 | 85 | 84 | 84 |

TABLE 2

|  |  | Com. Ex. 1 | Com. Ex. 2 | Com. Ex. 3 | Com. Ex. 4 | Com. Ex. 5 |
|---|---|---|---|---|---|---|
| Compositions | Polymerizable monomer A | 100 | 100 | 100 | 100 | 100 |
|  | Ground-type filler D | 150 |  |  |  |  |
|  | Ultrafine particle inorganic filler E |  | 150 | 100 |  |  |
|  | Ground-type filler F |  |  |  | 150 |  |
|  | Ground-type filler G |  |  |  |  | 150 |
| Properties | Flexural strength (MPa) | 151 | 78 | 69 | 156 | 155 |
|  | Gloss retention (%) | 58 | 68 | 89 | 65 | 56 |
|  | Transparency (ΔL) | 38 | 36 | 35 | 35 | 22 |
|  | Haze (%) | 45 | 51 | 54 | 48 | 73 |
|  | Total light transmittance (%) | 89 | 87 | 86 | 87 | 53 |

The results of Examples 1 to 5 show that the addition of the spherical inorganic filler leads to high flexural strength and excellent gloss retention. On the other hand, the gloss retention of Comparative Example 1 decreased, as shown in the result thereof. This is attributed to the irregular shape of the ground-type filler, which increased the surface roughness thereof. Both the flexural strength and the gloss retention of Comparative Example 2 decreased, as shown in the result thereof. This is attributed to the high content of the ultrafine particle inorganic filler, and thus the filler was not mixed with the polymerizable monomer well enough to obtain a homogeneous curable composition. In Comparative Example 3, the content of the ultrafine particle inorganic filler was reduced compared with that of Comparative Example 2. As a result, the homogeneity of the curable composition was obtained and thus adequate gloss retention was achieved, but the flexural strength further decreased due to a decrease in the content of the ultrafine particle inorganic filler. In Comparative Example 4, the gloss retention was slightly higher than that of Comparative Example 1 because the average primary particle The above results reveal that a dental mill blank having high flexural strength and excellent gloss retention can be obtained by curing a curable composition containing a spherical inorganic filler.

On the other hand, the results of Examples 6 to 9 reveal that a dental mill blank having high transparency, haze and total light transmittance and thus having improved color matching with natural teeth can be obtained by the combined use of a polymerizable monomer having a refractive index after polymerization in a specific range, a spherical inorganic filler having a refractive index in a specific range, and an inorganic ultrafine particle filler having a refractive index in a specific range.

Industrial Applicability

The dental mill blank of the present invention can be suitably used in the field of dental treatment to fabricate dental prostheses having high mechanical strength and excellent gloss retention by machining using a CAD/CAM system.

The invention claimed is:

1. A dental mill blank made of a cured product of a curable composition comprising:
   a polymerizable monomer (A); and
   filler,
   the filler consisting of
      a spherical inorganic filler (B) having an average particle size of not less than 0.1 μm and less than 1 μm and an inorganic ultrafine particle aggregate filler (C)) composed of aggregates of inorganic ultrafine particles having an average primary particle size of 2 to 50 nm.

2. The dental mill blank according to claim 1, wherein the spherical inorganic filler (B) is composed of silica particles; particles of an oxide of at least one metal selected from the group consisting of Group 2, Group 4, Group 12 and Group 13 metals of the periodic table; or particles of a composite oxide containing a silicon atom, an oxygen atom, and an atom of at least one metal selected from the group consisting of Group 2, Group 4, Group 12 and Group 13 metals of the periodic table.

3. The dental mill blank according to claim 1, wherein the polymerizable monomer (A) is a (meth)acrylic acid ester.

4. The dental mill blank according to claim 1, wherein the curable composition comprises 65 to 900 parts by weight of the spherical inorganic filler (B) per 100 parts by weight of the polymerizable monomer (A).

5. The dental mill blank according to claim 1, wherein
the polymerizable monomer (A) has a refractive index of 1.52 to 1.58 after polymerization, the spherical inorganic filler (B) has a refractive index of 1.52 to 1.58, and the inorganic ultrafine particle aggregate filler (C) has a refractive index of 1.43 to 1.50, and
a content of the inorganic ultrafine particle aggregate filler (C) in the curable composition is 0.1 to 10% by weight.

* * * * *